United States Patent [19]
Shain et al.

[11] Patent Number: 5,324,197
[45] Date of Patent: Jun. 28, 1994

[54] PORTABLE POWER SOURCE FOR DENTAL HANDPIECE ILLUMINATION

[76] Inventors: Nat R. Shain, 28751 Rancho Cal Rd., Temecula, Calif. 92590; Stan Lillard, 1043 Santo Antonio #124, Colton, Calif. 92324; Robert Lillard, 1882 Victoria Ave., San Bernardino, Calif. 92408

[21] Appl. No.: 14,716

[22] Filed: Feb. 8, 1993

[51] Int. Cl.$^5$ ............................................. A61C 3/00
[52] U.S. Cl. ........................................ 433/29; 433/98
[58] Field of Search ................... 433/29, 77, 98, 101

[56] References Cited

U.S. PATENT DOCUMENTS 3,072,738  1/1963  Epps, Jr. et al. .................... 433/29
3,077,665  2/1963  Saltzman .............................. 433/98
4,286,949  9/1981  Holt, Jr. .............................. 433/101
5,030,090  7/1991  Maeda et al. ......................... 433/29

Primary Examiner—John J. Wilson
Attorney, Agent, or Firm—James B. Middleton

[57] ABSTRACT

A portable power supply powers the light in a dental handpiece. The portable power supply includes a rechargeable battery for the electric power, and has connectors for connection to the handpiece and its fluid supply and exhaust. The connectors communicate with a manifold which has a port for connection of a pressure operated switch. The pressure operated switch operates the light so the light is illuminated only when the handpiece is operating.

4 Claims, 1 Drawing Sheet

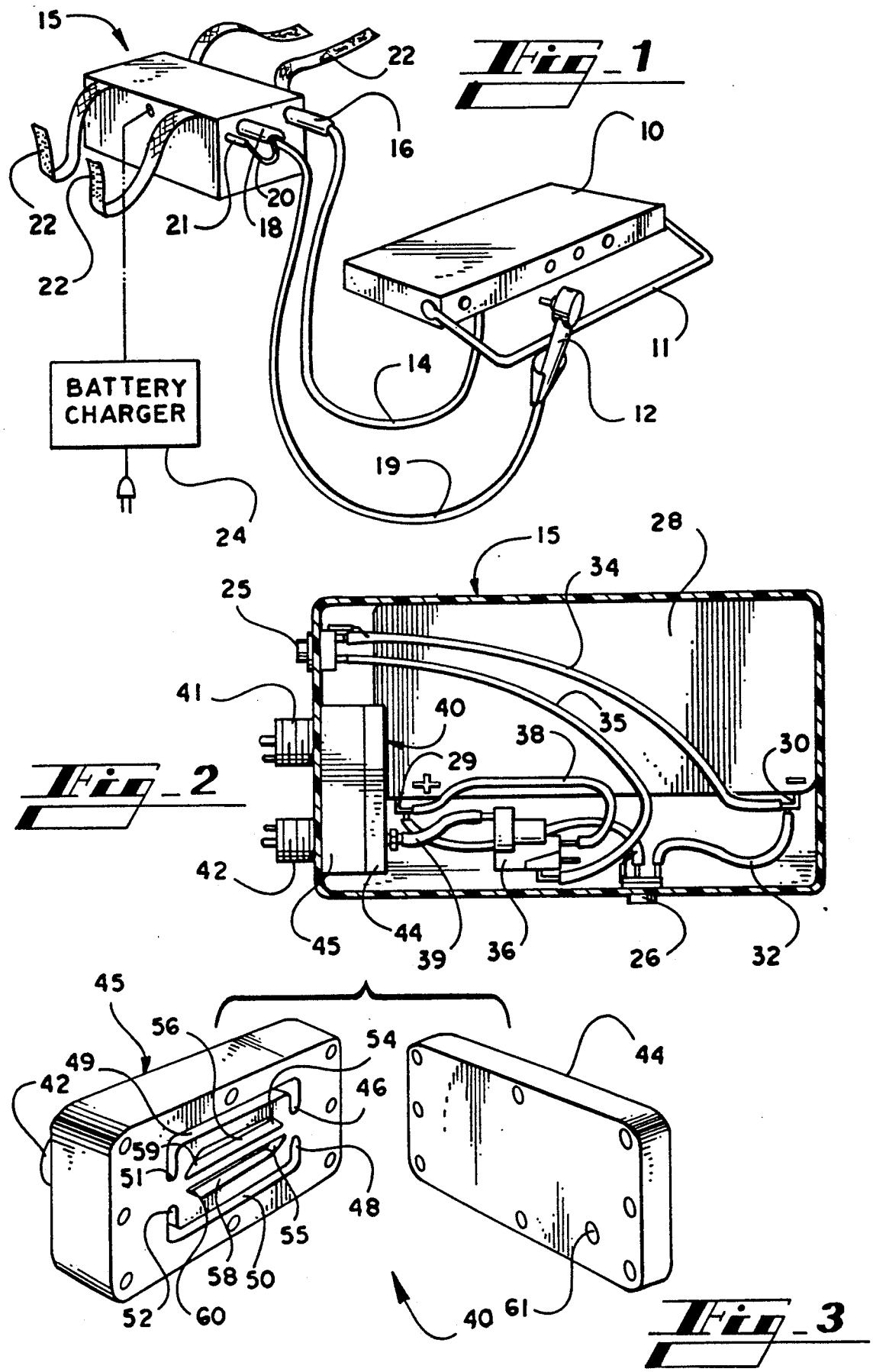

PORTABLE POWER SOURCE FOR DENTAL HANDPIECE ILLUMINATION

BACKGROUND OF THE INVENTION

1. Field of the Invention

This invention relates generally to dental handpieces, and is more particular concerned with a portable electric power source for the light on a dental handpiece.

2. Discussion of the Prior Art

The convention dental handpiece contains a turbine which is operated by gas under pressure. The usual handpiece also includes an electric light, the light from which is carried to the handpiece by fiber optics bundled with the tubes connected to the handpiece. The usual means for providing electric power to the light includes wiring that must be done by a skilled electrician, the wiring passing through the arm supporting the dental delivery unit, through the standard, and to a transformer on the floor. The transformer is then plugged into a conventional power outlet.

Those skilled in the art will understand that a dentist, or someone on the office staff, can move a dental handpiece from one station to another by simply unscrewing the connector from the delivery unit, and screwing the connector to the delivery unit where the handpiece is desired. However, the office personnel cannot move the power source for the light. Because of this, a dental office normally has a power source installed in each room wherein a handpiece will be used. This of course increases the cost of outfitting a dental office.

There has been some effort at providing a portable operating system for a dental handpiece, as shown by U.S. Pat. No. 4,286,949 to Holt, Jr. The Holt device, however, is concerned with a portable system that provides the handpiece, or drill, the syringe and a suction device, all in one unit. The Holt device would not be used in a normal dental office, but is designed to replace the entire delivery unit.

SUMMARY OF THE INVENTION

The present invention provides a portable power source for operating the light in a dental handpiece. The power source includes a battery for providing electric power, and means for energizing the light on actuation of the handpiece. The device of the present invention receives a line from the dental delivery unit, and provides a connection for the dental handpiece. A pressure operated switch provides for illumination of the light only when the handpiece is actuated. This allows the light on the handpiece to be operated as is normal, but from the portable power source.

BRIEF DESCRIPTION OF THE DRAWINGS

These and other features and advantages of the present invention will become apparent from consideration of the following specification when taken in conjunction with the accompanying drawings in which:

FIG. 1 is a perspective view showing a power source made in accordance with the present invention, and shown in conjunction with a conventional delivery unit;

FIG. 2 is a plan view of the power source shown in FIG. 1, the cover being cut away to show the interior; and, FIG. 3 is an exploded perspective view showing the manifold illustrated in FIG. 2.

DETAILED DESCRIPTION OF THE EMBODIMENT

Referring now more particularly to the drawings, and to that embodiment of the invention here presented by way of illustration, FIG. 1 rather schematically shows a conventional dental delivery unit 10. The delivery unit 10 includes a hanger 11 for receiving one or more handpieces 12. Conventionally, a line 14 is connected to the delivery unit 10, and to the handpiece 12. The line 19 comprises a plurality of tubes for carrying air and water to the handpiece, as well as the low voltage wires for carrying power to the lamp at the end of 19-A.

As illustrated in FIG. 1, the line 14 is connected to the power source 15 of the present invention. As will be discussed in more detail hereinafter, the power source 15 includes a conventional nipple for receiving the conventional connector 16. It will therefore be recognized that the line 14 provides fluid and air input to the power source 15.

Adjacent to the connector 16, there is another connector 18, the connector 18 being fixed to the line 19 which is connected to the handpiece 12. The power source 15 provides connecting means for connecting the fluid and air input from the line 14 to the fluid and air output into line 19. The handpiece 12 will therefore be operable in the usual fashion.

Those skilled in the art will realize that the connector 19 includes electric low voltage wires arranged to provide power into a lamp that is part of the line 19. To power this light, a cord 20 is provided, terminating in a plug 21.

It will be understood that the delivery unit 10 is carried on an arm which is not here shown. The power source 15 of the present invention can conveniently be attached to the same arm. Though many forms of attachment may be used, as here shown the power source 15 includes straps 22. The straps 22 are long enough to encircle the arm holding the delivery unit; and, the straps 22 may be fastened together with hook and loop fasteners or the like. The power source 15 is then easily and conveniently mounted adjacent to the delivery unit.

Attention is directed to FIG. 2 of the drawings for a detailed understanding of the power source 15. The power source 15 includes a battery 28 having positive and negative terminals 29 and 30. While many forms of battery might be used, it has been found that the sealed lead-acid battery is admirably suited to use with this invention. A 2 to 24 volt, lead-acid battery is easily rechargeable numerous times, and provides a significant amount of electric power with each charge.

The terminals 29 and 30 of the battery 28 are connected to a jack 26 by appropriate wires 31 and 32 so the battery 28 can be charged from the jack 26 by the battery charger 24.

There is a jack 25 which receives the plug 21 for the light to be operated with the handpiece. The jack 25 is connected by a wire 34 to the terminal 30 of the battery, and by a wire 35 to the common terminal of a pressure operated switch 36. The switch 36 has a normally open contact which is connected by a wire 38 to the terminal 29 of the battery 28. It will therefore be understood that, when the switch 36 is operated to complete the circuit between the common terminal and the normally open terminal, power will be supplied from the battery 28 to the jack 25.

Operation of the switch 36 is by air pressure, and the pressure is provided through a tube 39 from the manifold generally designated at 40.

The manifold 40 is here shown as having two nipples 41 and 42, the nipple 42 being adapted to receive the connector 16 to connect the line 14 to the delivery unit 10. The nipple 41 receives the connector 18 to connect the line 19 to the power source 15. It will therefore be understood that the primary purpose of the manifold 40 is to connect the individual ports in the nipple 41 with the equivalent ports in the nipple 42. Also, when there is pressure on the appropriate port, the pressure will be reflected through the tubing 39 to operate the switch 36.

Attention is directed to FIG. 3 of the drawings for a better understanding of the construction of the manifold 40. FIG. 3 shows the rear of the manifold 40, with the back plate 44 exploded therefrom.

Those skilled in the art will understand that the conventional connector for a dental handpiece includes four ports, and that the coupling of the screw connector 16 with the nipple 41 couples these four ports in a manner well known to those skilled in the art. The manifold 40 of the present invention is therefore designed to connect the two nipples 41 and 42, keeping the four ports appropriately differentiated. In the event a different number of ports is used, the manifold of the present invention would of course be adapted to the different number of ports, but the principle of the invention will be the same.

The manifold 40 includes a body 45 and the back plate 44. The body 45 has the nipples 41 and 42 extending there from, and defines a plurality of holes through the nipples 41 and 42 and through the body 45. Each of the holes through the body 45 is then connected with its equivalent hole by means of a groove. First, there are upper and lower holes in the nipple 41, these holes being designated in FIG. 3 at 46 and 48. The holes 46 and 48 are connected by grooves 49 and 50 respectively to holes 51 and 52 respectively. Similarly, the nipple 41 includes holes 54 and 55 which are connected by grooves 56 and 58 respectively to holes 59 and 60.

As shown in FIG. 3, the various grooves 49, 50, 56 and 58 are simply open grooves in the body 45 of the manifold 40. The back plate 44 will be received against the body 45 to close these grooves and provide closed channels for connecting the holes 46 and 51, 48 and 52, etc.

It will be noted that there is a hole 61 in the back plate 44. When the back plate 44 is appropriately received on the body 45, the hole 61 will be substantially aligned with the groove 50. As a result, when air pressure is admitted through the hole 52 and into the channel 50, the air under pressure in the channel 51 will cause operation of the pressure switch 36. If the installation of the manifold (40) in the portable power source (15) is reversed i. e. switch 41 to 42 by placing the manifold (40) upside down, then hole 61 will operate the pressure switch by means of the outgoing air exhaust.

With the above description in mind, operation of the portable power source should be understandable. With the delivery unit 10 installed in conventional fashion, the power source 15 will be fastened to the arm carrying the delivery unit. One of the lines, such as the line 14, will be connected to the nipple 42 by the connector 16. The handpiece 12 will then be connected to the nipple 41 on the power source 15 by the line 19 and connector 18. The plug will be inserted into the jack 25, and installation will be complete.

In use, when air under pressure is admitted to the nipple 42 through the line 14 and connector 16, the pressure will be conveyed through the various channels in the manifold 40 to the nipple 41; and, pressure on the chanel 50 will be reflected through the port 61, through the tubing 39 to operate the switch 36. When the switch 36 is operated, the terminals will be connected so that power will be supplied at the jack 25, and to the plug 21 to operate a light. All fluids received at the nipple 42 will be transferred through the manifold 40 to the nipple 41 for usual operation of the handpiece 12.

When the dental handpiece is to be moved, it will be understood that any dentist, dental assistant or the like can disconnect the connector 16 so the power source 15 is disconnected from the delivery unit. The straps 22 can be removed so the device 15 can be moved. Thus, the handpiece, with the portable power source, can be moved to a different location, and installed as discussed above. The present invention therefore provides a completely portable electric power source for a conventional dental handpiece illumination simple enough to install that any ordinary dental office personnel will be capable of installing the system.

It will of course be understood by those skilled in the art that the particular embodiment of the invention here presented is by way of illustration only, and is meant to be in no way restrictive; therefore, numerous changes and modifications may be made, and the full use of equivalents resorted to, without departing from the spirit or scope of the invention as outlined in the appended claims.

We claim:

1. A power source for a light in a dental handpiece, said dental handpiece being operated from a delivery unit, said delivery unit including a first handpiece line selectively connectable to said handpiece, said handpiece line comprising a plurality of tubes for carrying fluids and air to said handpiece, a light source, and low voltage wires for conducting low voltage electricity power from said source to said handpiece, said power source comprising a battery for providing electric power, a jack connected to said battery, a first nipple for connection of said one line, and a second nipple for connection of a second handpiece line, a second handpiece line including a plug, a cord connected to said plug and to said light source in said second handpiece line, said plug being receivable in said jack, a manifold for connecting said first nipple to said second nipple, a port defined in said manifold, and pressure operated switch means communicating with said port, and circuit means for connecting said switch means to said battery and to said jack.

2. A power source as claimed in claim 1, wherein said battery is a rechargeable battery, and further including a charging jack electrically connected to said battery, and a battery charger selectively connectable to said charging jack.

3. A power source as claimed in claim 2, said first nipple and said second nipple each defining a plurality of holes therethrough, said manifold defining a plurality of channels for connecting each hole of said first nipple with a hole in said second nipple.

4. A power source as claimed in claim 3, and further including strap means for mounting said power source adjacent to said delivery unit.

* * * * *